(12) United States Patent
Al-Rashdan

(10) Patent No.: US 8,795,219 B1
(45) Date of Patent: Aug. 5, 2014

(54) SYSTEM AND METHOD FOR REMOVING BLOOD CONTAINING CONTRAST DYE

(71) Applicant: Ibrahim Rashid Al-Rashdan, Qortoba (KW)

(72) Inventor: Ibrahim Rashid Al-Rashdan, Qortoba (KW)

( * ) Notice: Subject to any disclaimer, the term of this patent is extended or adjusted under 35 U.S.C. 154(b) by 0 days.

(21) Appl. No.: 14/218,726

(22) Filed: Mar. 18, 2014

Related U.S. Application Data

(60) Provisional application No. 61/801,690, filed on Mar. 15, 2013.

(51) Int. Cl.
*A61M 37/00* (2006.01)
*A61M 31/00* (2006.01)
*A61M 5/00* (2006.01)
*A61M 1/00* (2006.01)
*A61M 5/142* (2006.01)

(52) U.S. Cl.
CPC ............. *A61M 5/007* (2013.01); *A61M 1/0035* (2014.02); *A61M 5/142* (2013.01)
USPC .......................................... 604/6.1; 604/508

(58) Field of Classification Search
CPC ... A61M 1/0035; A61M 5/007; A61M 5/142; A61M 25/007; A61M 25/0068
USPC ....................... 604/4.01–6.16, 8–10, 507, 508
See application file for complete search history.

(56) References Cited

U.S. PATENT DOCUMENTS

| | | | |
|---|---|---|---|
| 4,820,261 A | 4/1989 | Schmoll et al. | |
| 5,411,479 A | 5/1995 | Bodden | |
| 5,919,163 A | 7/1999 | Glickman | |
| 6,554,819 B2 * | 4/2003 | Reich | 604/508 |
| 6,585,689 B1 | 7/2003 | Macoviak et al. | |
| 7,163,520 B2 | 1/2007 | Bernard et al. | |
| 7,824,357 B2 | 11/2010 | Al-Rashdan | |
| 2010/0274189 A1 | 10/2010 | Kurth et al. | |
| 2011/0172558 A1 | 7/2011 | Shapland et al. | |
| 2011/0251555 A1 | 10/2011 | Ducharme et al. | |

FOREIGN PATENT DOCUMENTS

WO    WO 02/060511 A2    8/2002

* cited by examiner

*Primary Examiner* — Philip R Wiest
(74) *Attorney, Agent, or Firm* — Richard C Litman

(57) ABSTRACT

The system for removing blood containing contrast dye includes an inner catheter having a fixed proximal end and a distal free end, and an outer catheter coaxially disposed around a portion of the inner catheter, defining an inner lumen and an annular outer lumen. The fixed end of the inner catheter is coincident with the proximal end of the outer catheter, and the distal end of the inner catheter extends outward from the outer catheter. A valve manifold provides a single operator control over the operation of the catheters and balloon in order to drain the dye from the coronary sinus system.

20 Claims, 3 Drawing Sheets

SYSTEM AND METHOD FOR REMOVING BLOOD CONTAINING CONTRAST DYE

CROSS-REFERENCE TO RELATED APPLICATION

This application claims the benefit of U.S. Provisional Patent Application Ser. No. 61/801,690, filed Mar. 15, 2013.

BACKGROUND OF THE INVENTION

1. Field of the Invention

This invention relates to the prevention of contrast-associated nephropathy, and particularly to a catheter and valve system and method for removing blood containing contrast dye.

2. Description of the Related Art

Percutaneous transluminal coronary angioplasty is frequently used in treating coronary atherosclerosis, which produces areas of blockage within a coronary artery. However, prior to performing percutaneous transluminal coronary angioplasty, and during the procedure itself, iodine containing dye or other contrast material is injected into a patient's coronary arteries through a catheter. This iodine solution is fluorescent and enables the coronary arteries to be clearly illustrated for the physician.

A serious problem associated with the use of such contrast solutions exists. The use of such solutions may lead to contrast-induced nephropathy. Contrast-induced nephropathy can result in transient or permanent renal impairment or failure of a patient's kidneys. It is well known that renal dysfunction is associated with the use of radiographic contrast media, and that the dysfunction may range from a transient slight increase in serum creatinine levels to renal failure requiring transient or long-term dialysis.

Many patients require revascularization of more than a single vessel. However, when there is danger of contrast-induced renal failure, the vessels are operated on in separate procedures at greatly increased cost and additional risk of arterial puncture. Therefore, it is highly desirable or imperative to eliminate the risk of renal failure.

Further, there are many other patients with chronic renal insufficiencies who must wait 24 to 48 hours in the hospital before undergoing percutaneous transluminal coronary angioplasty in order to space the kidney load associated with the contrast load. Still others, particularly the elderly with a pre-existing renal insufficiency, make up a large group in which angioplasty is avoided due to multi-vessel disease and multi-vessel intervention, which may lead to renal failure.

Contrast-induced nephropathy can be prevented if the contrast solution is kept away from the kidney. However, once the dye has been mixed with blood, the conventional method to separate the two is by filtration (for example, through dialysis). Dialysis relies on diffusion down a concentration gradient and is not completely effective if the concentration of dye in the blood to be filtered is low. Furthermore, the flow rates of conventional hemodialysis procedures are too high for patients who are undergoing angioplasty, and these patients typically do not tolerate wide fluctuations in blood pressure, as is common with hemodialysis.

Thus, A system and method for removing blood containing contrast dye solving the aforementioned problems is desired.

SUMMARY OF THE INVENTION

The system and method for removing blood containing contrast dye, such as radiographic contrast media used for angioplasty procedures, relates to the removal of blood containing contrast dye solution from the coronary sinus of the patient's heart before the blood containing the dye enters the right atrium and circulates through the bloodstream to the kidneys, potentially causing contrast-induced nephropathy (CIN). The system for removing blood containing contrast dye includes an inner catheter having opposed fixed and free ends, and an outer catheter. The inner catheter is partially disposed coaxially within the outer catheter, defining inner and outer lumens. The fixed proximal end of the inner catheter is positioned within the outer catheter, and the distal end of the inner catheter partially extends outward from the outer catheter. An annular suction orifice is defined between the outer catheter and the inner catheter at the distal end of the outer catheter. A guide may be further provided for covering the annular suction orifice and holding the inner catheter in place with respect to the outer catheter. The guide has openings or apertures formed therethrough, allowing blood containing the contrast dye to be suctioned therethrough.

A balloon is mounted on the outer catheter adjacent the annular suction orifice. The distal free end of the inner catheter extends beyond the balloon. An inflation line is in communication with the balloon. The inflation line terminates in a first inflation port. In use, the catheters, which have a curvature that facilitates the insertion of the system in the coronary sinus, are inserted into the coronary sinus, the outer catheter extending to the ostium and the inner catheter extending into the sinus. The balloon is inflated after introducing a contrast solution into a patient's blood stream. Blood containing contrast solution from between the first and second balloons is then removed. The second balloon is inflated first in order to anchor the inner catheter in place in the coronary sinus, the free end thereof being positioned adjacent the patient's lateral vein. Preferably, the inner catheter is formed from a softer material than the outer catheter, thus allowing the outer catheter to be used for positioning, and preventing damage to the inner wall of the coronary sinus vein.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The system and method for removing blood containing contrast dye maximizes the filtration of contrast solution from the blood by placing a catheter in the coronary sinus where the concentration of contrast dye is the highest. The catheter is provided with means for blocking the flow of blood to the right atrium, while simultaneously permitting the blood in the coronary sinus to be delivered through the catheter to a filtration machine. The way in which this is accomplished is explained with reference to FIG. 1, which illustrates a heart in which a catheter 10 has been introduced from the groin, then through the inferior vena cava (IVC) into the coronary sinus (CS). The distal portion of the catheter 10 carries a balloon 12, which can be inflated and deflated as required. Balloon catheters are well known and, therefore, the actual catheter construction is not described in detail. In addition to balloon 12, catheter 10 also includes a port, defined by a porting inner catheter 14, distal but close to the balloon 12, which permits blood in the coronary sinus to drain into the catheter lumen when the balloon 12 occludes the coronary sinus.

Figure 2:
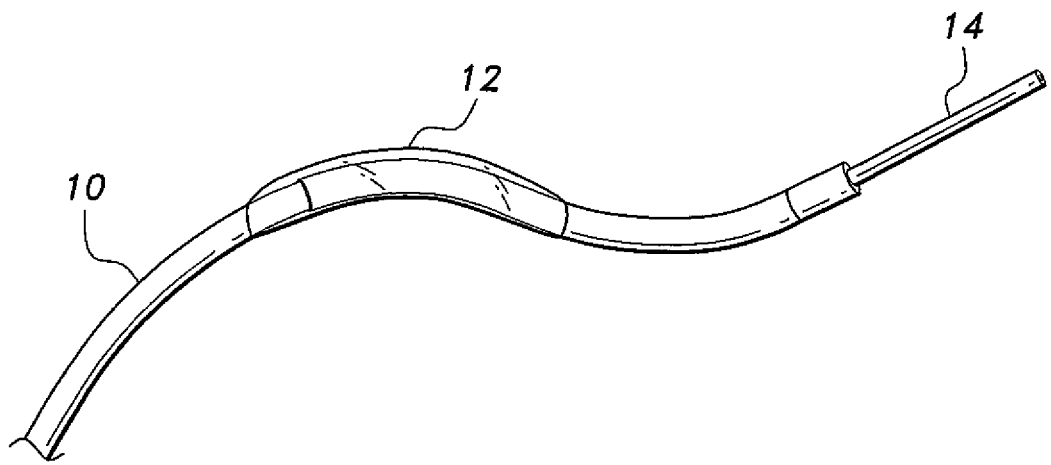
FIG. 2 is a perspective view of a balloon catheter of the system of FIG. 1, shown with the balloon deflated.
Figure 3:
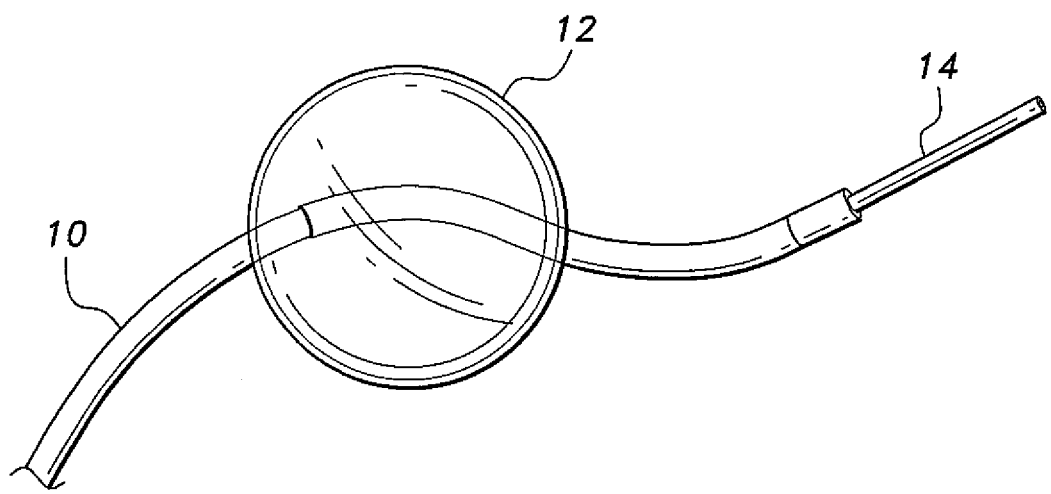
FIG. 3 is a perspective view of the balloon catheter of FIG. 2, shown with the balloon inflated.

FIGS. 2 and 3 show structure of the catheter 10 in a perspective view. The catheter 10 is preferably positioned with its tapered distal end distal of the coronary sinus and balloon 12, which is expanded to block blood flow from the coronary sinus to the right atrium. The catheter 10 has an outer diameter on the order of 8 Fr (French). Internal to the catheter 10, an inner guide catheter 14 is shown at the distal end of catheter 10, the inner guide catheter having a diameter on the order of 4 Fr. In other words, the catheter 10 is a double lumen catheter in which the lumens are coaxial, the inner guide catheter 14 defining an inner lumen and the annular space between the inner guide catheter 14 and the outer catheter defining an annular outer lumen. The inner guide catheter 14 provides the porting for the contrast dye being used in the patient evaluations. The balloon 12 is shown deflated in FIG. 2, at which state the catheter will be introduced or retracted from the patient. FIG. 3 shows the balloon 12 inflated, which is the state at allowing for the occlusion of the coronary sinus. The function of the single balloon catheter is well known, and is used in conjunction with the valve system of FIG. 4.

Figure 1:
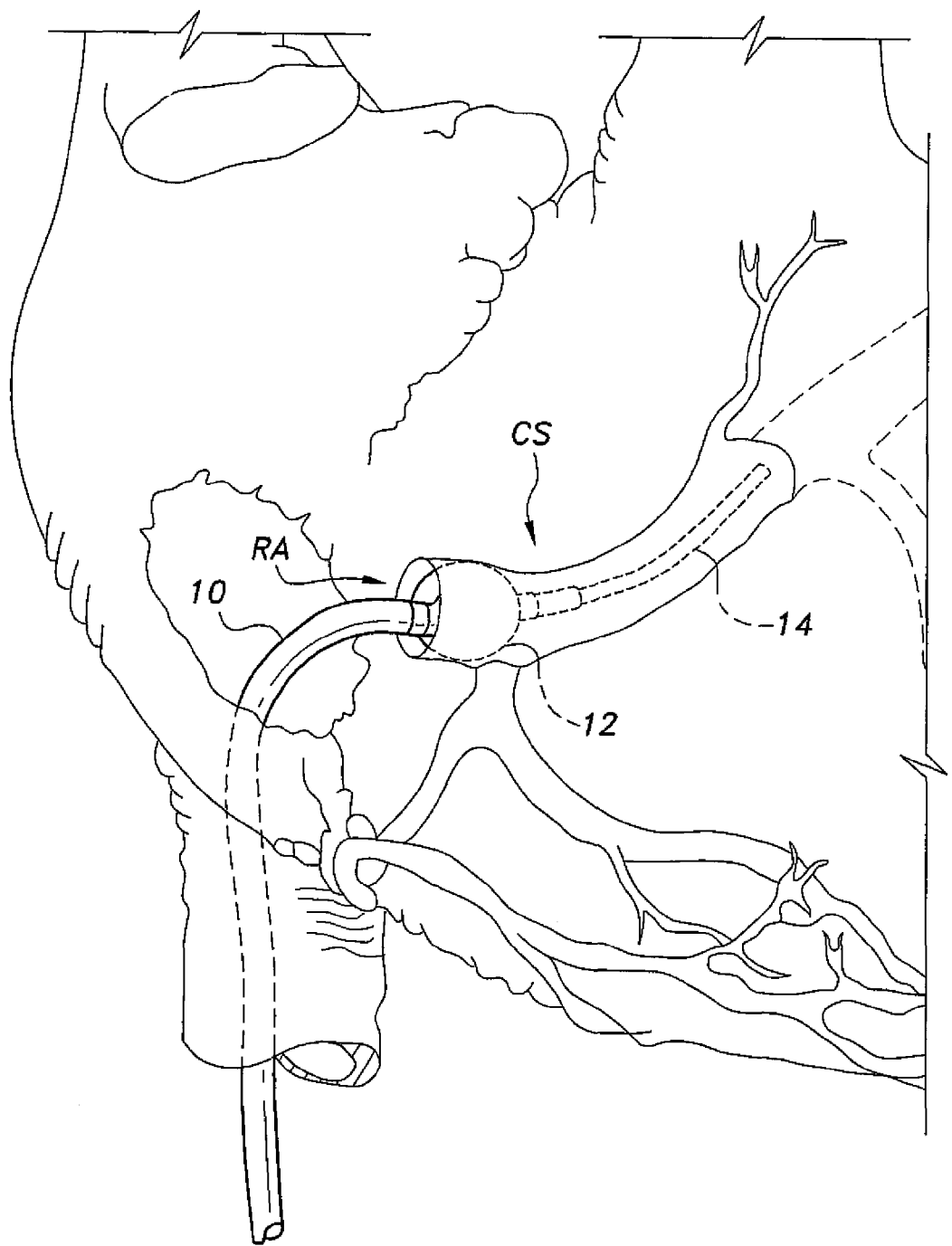
FIG. 1 is an environmental partial perspective view diagrammatically illustrating a system for removing blood containing contrast dye according to the present invention.
Figure 4:
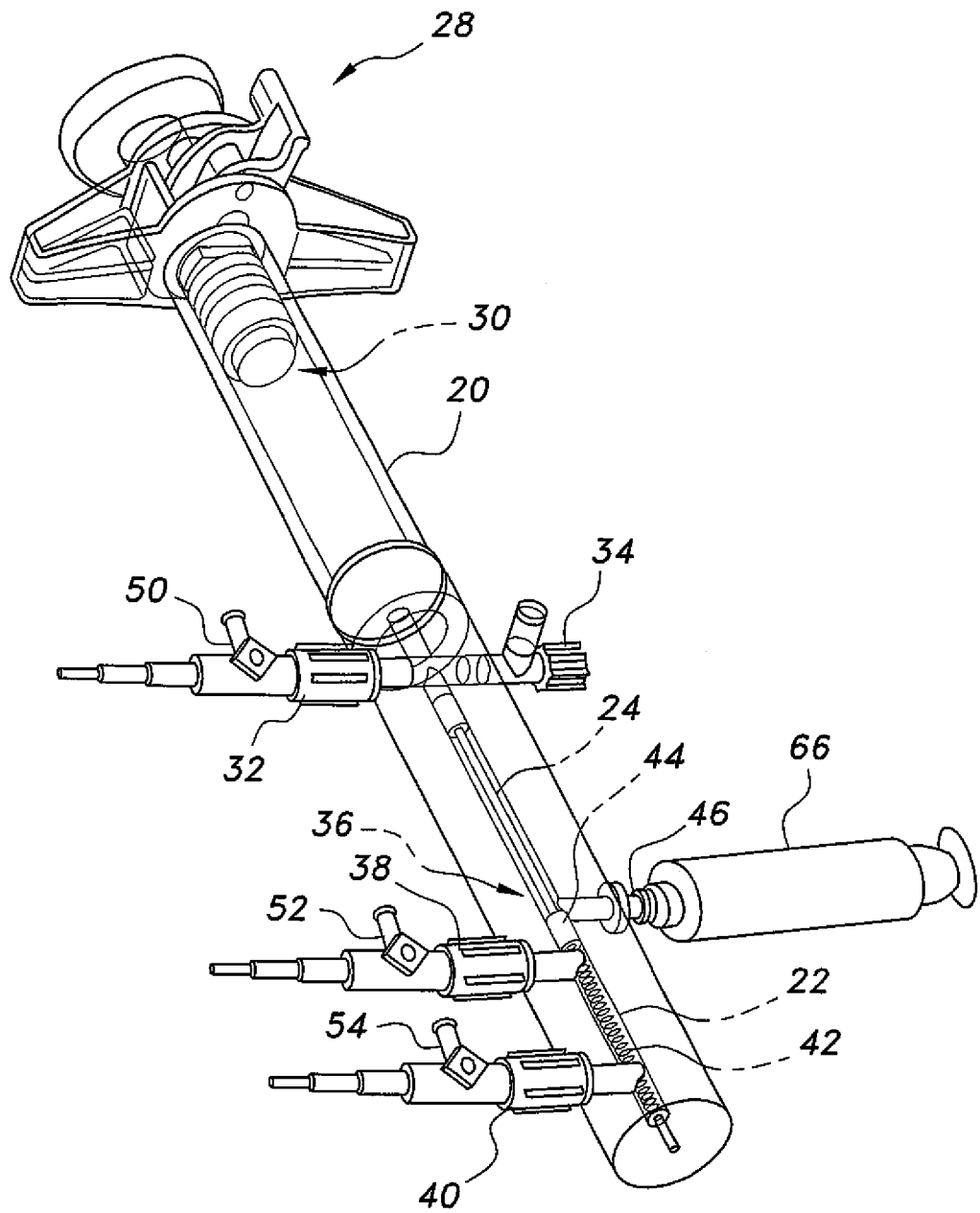
FIG. 4 is a perspective view of a valve assembly of the system for removing blood containing contrast dye of FIG. 1.

FIG. 4 shows a valve assembly structure intended for operation by a single user, for use with the catheters 10 and 14 of FIGS. 1-3. The valve assembly has a manifold 20 and a piston drive (or plunger) 30 slidable in the manifold 20 for producing the necessary positive and negative pressures to the catheters 10, 14. The piston drive (or plunger) 30 is a manually operated pressure inducer for inflating and deflating the balloon 12. Within the manifold 20, a conduit 22 is connected to various ports, as will be described in detail below. Within the conduit 22, a sliding dual headed plunger 24 provides seals between the various ports for fluid engagement with the catheters 10, 14 and the balloon 12. The manifold 20 has a first port 32 for introducing and removing the fluid (e.g., air or saline) to the balloon 12. Associated with the first port 32 is a second port 34, serving as a pressure relief port for maintaining a safe pressure of the balloon 12 within the blood vessels of the patient.

Third and fourth ports 38 and 40, respectively, are provided for aspiration of the catheters 10, 14. Ports 38, 40 extract the contrast dye from the catheters 10, 14. The third and fourth ports 38, 40 function along with dual headed plunger 24 within the manifold conduit 22. A fifth port 46 provides a vacuum connection. The vacuum is provided via a collection syringe 66, or a negative pressure source to aid in the aspiration of the dye to be collected. The manifold 20 provides a single operator the ability to control inflation and deflation of the balloon 12, as well as to aspirate contrast dye from the blood vessels.

The manifold 20 also includes a locking mechanism 28 for sustaining the piston drive (or plunger) 30 in a selected position for affording the operator the ability to facilitate the various functions during the dye drainage procedures. The spring-biased dual-headed plunger 24 is designed and configured to maintain a fluid seal across the aspirators. Attached to the first, third, and fourth ports 32, 38, 40 are respective three-way stop cocks 50, 52, 54. Each stop cock provides a specific function when used in conjunction with the manifold 20.

In use, the first port 32, along with its three-way stop cock 50, are attached to the balloon inflation line. A vacuum syringe 66 is attached to the fifth vacuum port 46. The plunger 30 is moved so that all air is removed from the balloon 20 inflation line and the syringe 66. Once this preparation has been accomplished, the vacuum syringe 66 is used to apply maximum negative pressure to the internal conduit 22, and the syringe 66 is then locked in place. All three stop cocks 50, 52, 54 are secured in their respective first position. Contrast dye is then injected into the coronary arteries, and the balloon 12 is inflated by depressing the piston drive (or plunger) 30 of the manifold 20. Any excess pressure in the balloon inflation line will be expelled via the pressure relief port 34.

By depressing the piston drive (or plunger) 30, the dual headed plunger 24 is forced along the internal conduit 22 of the manifold 20, becoming aligned with the third and fourth aspiration ports 38, 40 and compressing the spring 42. In this position, a vacuum is automatically activated through the outer and inner catheters 10, 14. The syringe 66 will collect the dye that has been aspirated via the catheters 10, 14, and the piston drive (or plunger) 30 is moved in an opposite direction. Once retracted, the piston drive (or plunger) 30 relieves the pressure in the manifold 20 and deflates the balloon 12. Simultaneously, the dual-headed plunger 24 is spring-biased within the conduit 22 and seals the aspirator ports 38, 40. The syringe 66, now filled with the dye drained from the sinus system, may be removed, emptied, and returned to continue the dye draining process.

During operation, when the contrast dye is not being removed, the three-way stop cocks 52, 54 on the third and fourth ports 38, 40 are positioned to allow a slight blood drip, thereby preventing clotting within the dye drain system lumens. It should be understood that the contrast dye drain system provides a manifold 20 that allows a single operator to inflate the balloon 12 and simultaneously drain the dye from the coronary sinus system without having to monitor a separate pressure measuring system for the applied pressure. The manifold 20 provides a structure that affords easy connections for the ports. The manifold 20 is easily reset for multiple withdrawals within one single procedure. The manifold 20 is also fabricated of materials that make it cost effective for ready disposal. Likewise, manifold 20 may be manufactured from materials that provide for the reuse of the system after appropriate cleaning and sterilization.

It is to be understood that the present invention is not limited to the embodiments described above, but encompasses any and all embodiments within the scope of the following claims.

I claim:

1. A system for removing blood containing contrast dye, comprising:

an outer catheter having opposed proximal and distal ends;

an inner catheter coaxially disposed within the outer catheter, the inner catheter having a proximal end and a distal end projecting from the distal end of the outer catheter, the inner catheter defining an inner lumen, an annular outer lumen being defined between the inner catheter and the outer catheter;

a selectively inflatable balloon mounted on the outer catheter adjacent the distal end thereof;

a valve assembly manifold having first, second, third and fourth ports, the selectively inflatable balloon being in releasable fluid communication with the first port through an inflation line, the proximal end of the outer catheter being in releasable fluid communication with the second port for selective aspiration of the outer lumen, and the proximal end of the inner catheter being in releasable fluid communication with the third port for selective aspiration of the inner lumen;

means for selectively inflating and deflating the selectively inflatable balloon in fluid communication with the manifold;

a conduit mounted within the manifold, the conduit being in fluid communication with the first, second, third and fourth ports;

a dual-headed plunger slidably disposed within the conduit for selectively and releasably sealing the first, second and third ports, the plunger being slidable between a first position sealing the second and third ports from communication with the fourth port, and a second position placing the second and third ports in fluid communication with the fourth port; and means for selectively providing negative pressure within the conduit through the fourth port, wherein, contrast dye is injectable into coronary arteries of a patient through the inner and outer catheters when the plunger is in the first position, the plunger being moved to the second position when the balloon is inflated in the coronary sinus so that negative pressure applied to the fourth port aspirates the contrast dye through the inner and outer lumens and through the second and third ports into the conduit for removal through the fourth port, the plunger returning to the first position when the balloon is deflated.

2. The system for removing blood containing contrast dye as recited in claim 1, wherein said outer catheter has an outer diameter of about 8 Fr.

3. The system for removing blood containing contrast dye as recited in claim 2, wherein said inner catheter has an outer diameter of about 4 Fr.

4. The system for removing blood containing contrast dye as recited in claim 1, wherein said means for selectively inflating and deflating the selectively inflatable balloon comprises a plunger slidably disposed within said manifold.

5. The system for removing blood containing contrast dye as recited in claim 4, further comprising means for selectively locking the plunger within said manifold.

6. The system for removing blood containing contrast dye as recited in claim 1, wherein said manifold further includes a pressure relief port in fluid communication with the first port.

7. The system for removing blood containing contrast dye as recited in claim 1, wherein said means for selectively providing negative pressure within said manifold comprises a syringe in fluid communication with the fourth port.

8. The system for removing blood containing contrast dye as recited in claim 1, further comprising a first valve for selectively controlling fluid flow through the first port.

9. The system for removing blood containing contrast dye as recited in claim 8, further comprising a second valve for selectively controlling fluid flow through the second port.

10. The system for removing blood containing contrast dye as recited in claim 9, further comprising a third valve for selectively controlling fluid flow through the third port.

11. A valve system for removing blood containing contrast dye, comprising:

a manifold having first, second, third and fourth ports, the first port being adapted for fluid communication with a selectively inflatable balloon of a balloon catheter, the second port being adapted for communication with a proximal end of an outer catheter of the balloon catheter for selective aspiration thereof, and the third port being adapted for communication with a proximal end of an inner catheter of the balloon catheter for selective aspiration thereof;

means for selectively inflating and deflating the selectively inflatable balloon in fluid communication with the manifold;

a conduit mounted within the manifold, the conduit being in fluid communication with the first, second, third and fourth ports;

a sliding, dual-headed plunger received within the conduit for selectively and releasably sealing the first, second and third ports; and means for selectively providing negative pressure within the conduit through the fourth port, whereby negative pressure is initially applied to the conduit and contrast dye is injected into coronary arteries of a patient through the inner and outer catheters, the balloon being inflated such that when the contrast dye is to be removed, the sliding, dual-headed plunger is brought into alignment with the third and fourth ports to generate negative pressure within the inner and outer catheters for removing blood containing the contrast dye, the blood containing the contrast dye being drained through the fourth port, the balloon then being deflated while the second and third ports are sealed by the sliding, dual-headed plunger.

12. The valve system for removing blood containing contrast dye as recited in claim 11, wherein said outer catheter has an outer diameter of about 8 Fr.

13. The valve system for removing blood containing contrast dye as recited in claim 12, wherein said inner catheter has an outer diameter of about 4 Fr.

14. The valve system for removing blood containing contrast dye as recited in claim 11, wherein said means for selectively inflating and deflating the selectively inflatable balloon comprises a plunger slidably disposed within said manifold.

15. The valve system for removing blood containing contrast dye as recited in claim 14, further comprising means for selectively locking the plunger within said manifold.

16. The valve system for removing blood containing contrast dye as recited in claim 11, wherein said manifold further includes a pressure relief port in fluid communication with the first port.

17. The valve system for removing blood containing contrast dye as recited in claim 11, wherein said means for selectively providing negative pressure within said manifold comprises a syringe in fluid communication with the fourth port.

18. The valve system for removing blood containing contrast dye as recited in claim 11, further comprising a first valve for selectively controlling fluid flow through the first port.

19. The valve system for removing blood containing contrast dye as recited in claim 18, further comprising a second valve for selectively controlling fluid flow through the second port.

20. The valve system for removing blood containing contrast dye as recited in claim 19, further comprising a third valve for selectively controlling fluid flow through the third port.

* * * * *